(12) United States Patent
Benett et al.

(10) Patent No.: US 8,778,663 B2
(45) Date of Patent: Jul. 15, 2014

(54) THERMAL CYCLER

(75) Inventors: William J. Benett, Livermore, CA (US);
John T. Andreski, Tracy, CA (US);
John M. Dzenitis, Danville, CA (US);
Anthony J. Makarewicz, Livermore, CA (US); Dean R. Hadley, Manteca, CA (US); Satinderpall S. Pannu, Pleasanton, CA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 1495 days.

(21) Appl. No.: 11/901,787

(22) Filed: Sep. 18, 2007

(65) Prior Publication Data
US 2009/0074628 A1   Mar. 19, 2009

(51) Int. Cl.
*C12M 1/00*       (2006.01)
*C12M 3/00*       (2006.01)
*B01L 7/00*       (2006.01)
*C12Q 1/68*       (2006.01)
*B01L 3/00*       (2006.01)

(52) U.S. Cl.
CPC .............. *B01L 7/52* (2013.01); *C12Q 1/6844* (2013.01); *C12M 41/14* (2013.01); *B01L 3/50851* (2013.01); *B01L 2200/147* (2013.01)
USPC ...... 435/285.1; 435/6.1; 435/286.1; 422/138; 422/307

(58) Field of Classification Search
CPC ...... C12Q 1/686; C12Q 1/6844; C12Q 1/689; C12Q 1/6853; C12Q 1/6848; C12Q 1/6879; B01L 7/52; B01L 2200/147; B01L 3/50851; C12M 41/48; C12M 41/14; C12M 35/00; C12M 35/02; G06F 19/18
USPC ...................... 422/131, 132; 435/285.1, 285.6
See application file for complete search history.

(56) References Cited

U.S. PATENT DOCUMENTS

| | | | |
|---|---|---|---|
| 5,241,363 A | 8/1993 | Garner | |
| 5,589,136 A | 12/1996 | Northrup et al. | |
| 5,779,981 A | 7/1998 | Danssaert et al. | |
| 5,795,720 A * | 8/1998 | Henco et al. ................. | 435/6.12 |
| 6,509,186 B1 | 1/2003 | Zou et al. | |
| 6,762,049 B2 | 7/2004 | Zou et al. | |
| 2001/0036672 A1 * | 11/2001 | Anderson et al. ............. | 436/180 |
| 2003/0104590 A1 | 6/2003 | Santini et al. | |
| 2004/0072334 A1 | 4/2004 | Benett et al. | |
| 2005/0002024 A1 | 1/2005 | Green | |
| 2006/0029963 A1 * | 2/2006 | Billing-Medel et al. .......... | 435/6 |

FOREIGN PATENT DOCUMENTS

WO   WO 2004/018105   3/2004

* cited by examiner

*Primary Examiner* — Michael Hobbs
(74) *Attorney, Agent, or Firm* — Eddie E. Scott

(57) ABSTRACT

A thermalcycler includes a first thermalcycler body section having a first face and a second thermalcycler body section having a second face. A cavity is formed by the first face and the second face. A thermalcycling unit is positioned in the cavity. A heater trace unit is connected to a support section, to the first thermalcycler body section, to the second thermalcycler body section, and to the thermalcycling unit. The first thermalcycler body section and the second thermalcycler body section are positioned together against the support section to enclose the thermalcycling unit and the heater trace unit.

20 Claims, 11 Drawing Sheets

THERMAL CYCLER

STATEMENT AS TO RIGHTS TO INVENTIONS MADE UNDER FEDERALLY SPONSORED RESEARCH AND DEVELOPMENT

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to thermocyclers and more particularly to a thermalcycler for various operations including polymerase chain reactions, testing for DNA hybridization, isothermal reactions, nucleic acid sequence-based amplification, rolling-circle amplification, incubation for immunoassays, and other uses.

2. State of Technology

U.S. Pat. No. 5,779,981 for a thermal cycler including a temperature gradient block provides the following state of technology information:

"Systems which require multiple or cyclic chemical reactions to produce a desired product often require careful temperature control to produce optimal results. Such reactions include nucleic acid amplification reactions such as the polymerase chain reaction (PCR) and the ligase chain reaction (LCR). For this reason, apparatus have been developed which permit the accurate control of the temperature of reaction vessels in which such amplification reactions are performed.

For example, there are a number of thermal 'cyclers' used for DNA amplification and sequencing in the prior art in which one or more temperature controlled elements or 'blocks' hold the reaction mixture, and the temperature of a block is varied over time.

The PCR technique typically involves the step of denaturing a polynucleotide, followed by the step of annealing at least a pair of primer oligonucleotides to the denatured polynucleotide, i.e., hybridizing the primer to the denatured polynucleotide template. After the annealing step, an enzyme with polymerase activity catalyzes synthesis of a new polynucleotide strand that incorporates the primer oligonucleotide and uses the original denatured polynucleotide as a synthesis template. This series of steps (denaturation, primer annealing, and primer extension) constitutes a PCR cycle. As cycles are repeated, the amount of newly synthesized polynucleotide increases geometrically because the newly synthesized polynucleotides from an earlier cycle can serve as templates for synthesis in subsequent cycles. Primer oligonucleotides are typically selected in pairs that can anneal to opposite strands of a given double-stranded polynucleotide sequence so that the region between the two annealing sites is amplified.

The temperature of the reaction mixture must be varied during a PCR cycle, and consequently varied many times during a multicycle PCR experiment. For example, denaturation of DNA typically takes place at around 90°-95° C., annealing a primer to the denatured DNA is typically performed at around 40°-60° C., and the step of extending the annealed primers with a polymerase is typically performed at around 70°-75° C. Each of these steps has an optimal temperature for obtaining the desired result. Many experiments are required to determine the optimal temperature for each step.

For example, while the temperature at which DNA denatures is generally between 90°-95° C., slight variations in the particular temperature necessary are observed depending on the length of the DNA and the percentage of each of the four deoxynucleotides present (guanine-cytosine pairs and adenine-thymine pairs). Insufficient heating during the denaturation step is a common reason for a PCR reaction to fail. However, overheating during the denaturation step can result in excessive denaturation of the polymerase.

Achieving the optimal temperature for the PCR annealing step is even more critical. An annealing temperature which is too low will result in non-specific DNA fragments being amplified. At too high of an annealing temperature, the primers will anneal less efficiently resulting in decreased yield of the desired product and possibly reduced purity. In the annealing step, the optimal temperature will depend on many factors including the length of the primer and the percentage of each of the four deoxynucleotides present (guanine-cytosine pairs and adenine-thymine pairs). For a typical 20-base oligonucleotide primer comprised of roughly 50% guanine-cytosine, a temperature of 55° C. is a good estimate for the lower end of the temperature range. However, as one increases the primer length in order to attain greater primer specificity, differing annealing temperatures may be required. Thus, the number of subtle influences on the optimal annealing temperature makes difficult the task of quickly identifying the optimum for a given system.

Achieving the optimal temperature for the extension reaction is also important for obtaining the desired PCR result. Temperature may affect both the rate and the accuracy of the extension reaction. If the rate of the polymerase reaction is too low, then the newly synthesized polynucleotide may not contain a site for primer annealing. Additionally, the denatured polynucleotide sequence for amplification may contain one or more regions of secondary structure that may form or disappear according to the temperature selected. Furthermore, several different enzymes with polymerase activity may be used for PCR. Each enzyme will have its own optimum temperature for activity, stability and accuracy.

Determination of the optimal denaturing, annealing, and extension temperatures for a particular PCR is complicated by the fact that the optimum will be different for each of the reactions. Thus, in order to determine the three optimal temperature ranges, multiple separate experiments must be run where two temperature variables are held constant while a third temperature variable is changed. As a result, determination of the optimal temperature for running a PCR system can be a time consuming task."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a thermalcycler including a first thermalcycler body section having a first face and a second thermalcycler body section having a second face. The first thermalcycler body section and the second thermalcycler body section are made of a material that is a good thermal conductor. A cavity is formed by the first face and the second face. A thermalcycling unit is positioned in the cavity. A support section supports the first thermalcycler body section and the second thermalcycler body section. A heater trace unit is connected to the support section, to the first thermalcycler body section, to the second thermalcycler body section, and to the thermalcycling unit. The first thermalcycler body section and the second thermalcycler body section are positioned together against the support section to enclose the thermalcycling unit and the heater trace unit.

The present invention also provides a method of constructing a thermalcycler. The method includes various steps. A polyimide film support section is provided. A first thermalcycler body section having a first face is provided. The first thermalcycler body section is made of a material that is a good thermal conductor. A second thermalcycler body section having a second face is provided. The second thermalcycler body section is made of a material that is a good thermal conductor. A cavity is formed in at least one of the first face or the second face. A heater trace unit is connected to the support section, to the first thermalcycler body section, to the second thermalcycler body section, and to the thermalcycling unit. A thermalcycler unit is operatively connected to the cavity, to the polyimide film support section, and to the heater trace unit. The first thermalcycler body section, the second thermalcycler body section, and the polyimide film support section are positioned together wherein the first face and the second face are opposed to each other enclosing the heater trace unit and the thermalcycler unit.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
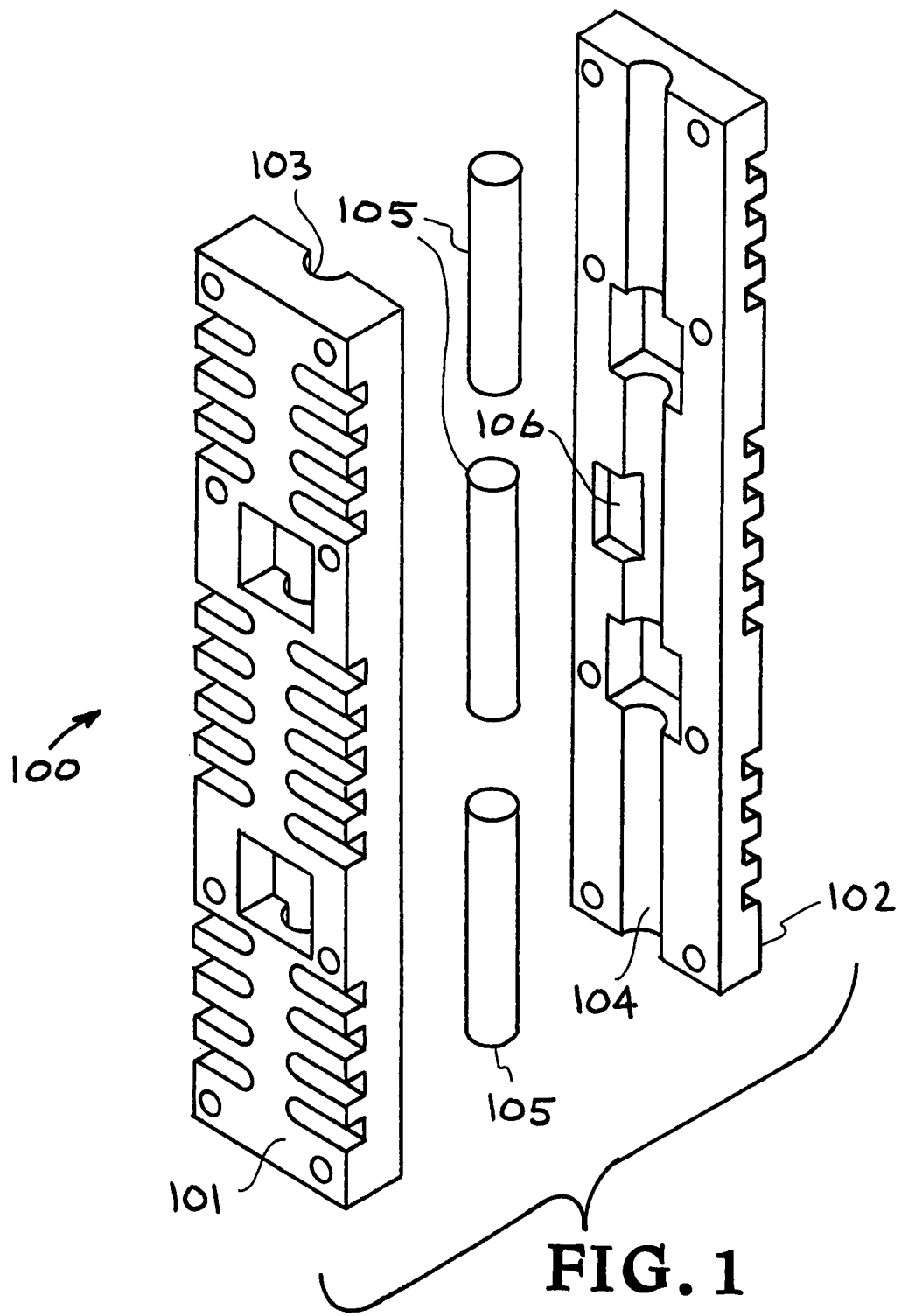
FIGS. 1 through 7 illustrate the structural details and the operation of one embodiment of a thermalcycling system constructed in accordance with the present invention.

Referring now to the drawings, to the following detailed information, and to incorporated materials; a detailed description of the invention, including specific embodiments, is presented. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention provides a thermalcycler for various operations including polymerase chain reaction, testing for DNA hybridization, isothermal reaction, nucleic acid sequence-based amplification, rolling-circle amplification, incubation for immunoassay, and other uses.

Referring now to FIGS. 1 through 7, the structural details and the operation of an embodiment of a thermalcycling system constructed in accordance with the present invention is illustrated. This embodiment of a thermalcycling system is designated generally by the reference numeral 100. This embodiment provides a thermalcycler for various operations including polymerase chain reaction, testing for DNA hybridization, isothermal reaction, nucleic acid sequence-based amplification, rolling-circle amplification, incubation for immunoassay, and other uses.

The thermalcycling system 100 includes a first thermalcycler body section having a first face and a second thermalcycler body section having a second face. The first thermalcycler body section and the second thermalcycler body section are made of a material that is a good thermal conductor. Good thermal conductors are things like: metals (iron, aluminum, copper, steel, titanium, etc. Good thermal conductors heat up and cool down very quickly.

A cavity is formed by the first face and the second face. A thermalcycling unit is positioned in the cavity. A heater trace unit is connected to the support section, to the first thermalcycler body section, to the second thermalcycler body section, and to the thermalcycling unit. The first thermalcycler body section and the second thermalcycler body section are positioned together against the support section to enclose the thermalcycling unit and the heater trace unit.

In one embodiment a Resistance Temperature Detector (RTD) is integrated into the thermalcycler. In one embodiment the thin film heater material is a nickel alloy. The heater pattern is made by using photolithography to create a mask on the nickel alloy film. An etchant is used to etch away all the material except where it is protected by the masking material.

The thermalcycling system 100 also provides a method of constructing a thermalcycler. The method includes various steps. A polyimide film support section is provided. A first thermalcycler body section having a first face is provided. The first thermalcycler body section is made of a material that is a good thermal conductor. A second thermalcycler body section having a second face is provided. The second thermalcycler body section is made of a material that is a good thermal conductor. A cavity is formed in at least one of the first face or the second face. A heater trace unit is connected to the support section, to the first thermalcycler body section, to the second thermalcycler body section, and to the thermalcycling unit. A thermalcycler unit is operatively connected to the cavity, to the polyimide film support section, and to the heater trace unit. The first thermalcycler body section, the second thermalcycler body section, and the polyimide film support section are positioned together wherein the first face and the second face are opposed to each other enclosing the heater trace unit and the thermalcycler unit.

Referring specifically to FIG. 1, the thermalcycling system 100 is made of a pair of mirror image body sections. The mirror image body sections are first thermalcycler body section 101 and second thermalcycler body section 102. The first thermalcycler body section 101 and the second thermalcycler body section 102 are made of a material that is a good thermal conductor. The material that is a good thermal conductor has thermal conductivity. Wikipedia, the free encyclopedia defines "thermal conductivity." In physics, thermal conductivity, k, is the intensive property of a material that indicates its ability to conduct heat. It is defined as the quantity of heat, Q, transmitted in time t through a thickness L, in a direction normal to a surface of area A, due to a temperature difference ΔT, under steady state conditions and when the heat transfer is dependent only on the temperature gradient. Prior art thermal cyclers were constructed from silicon.

The first thermalcycler body section 101 and the second thermalcycler body section 102 are copper chamber halves. Copper provides good thermal conductivity. The first and second body sections 101 and 102 have cavities 103 and 104 respectively. The cavities 103 and 104 receive copper guide tubes 105.

Figure 2:
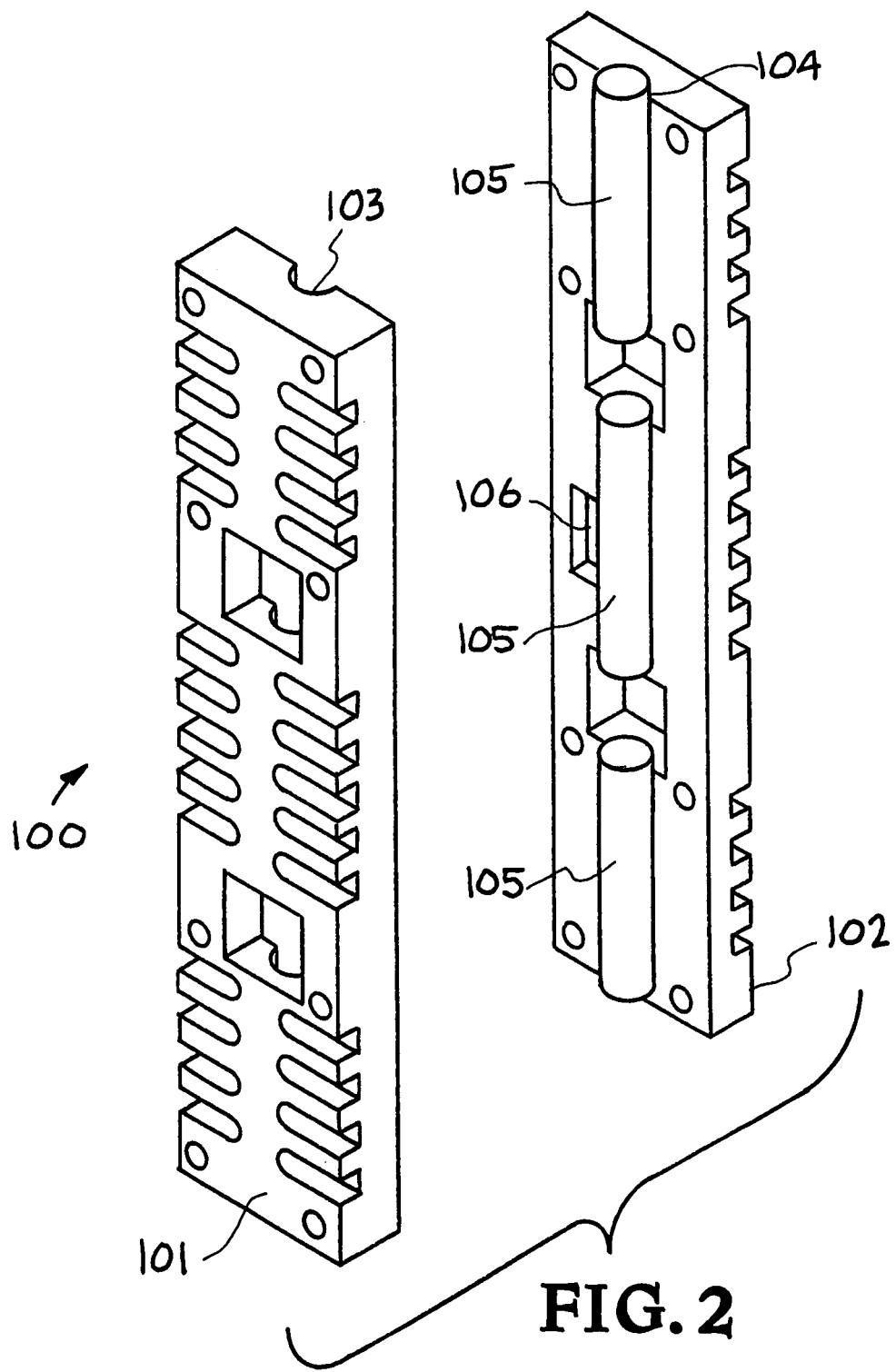

Referring specifically to FIG. 2, the first copper chamber half 101 and the second copper chamber half 102 receive the copper guide tubes 105. The first copper chamber half 101 includes cavity 103. The second copper chamber half 102 includes cavity 104. As illustrated in FIG. 2, the first copper chamber half 101 is illustrated in position for receiving the copper guide tubes 105 in the cavity 103. In a similar manner, when the first copper chamber half 101 and the second copper chamber half 102 are assembled together the second copper chamber half 102 will receive the copper guide tubes 105 in the cavity 102. A pocket 106 for a Resistance Temperature Detectors (RTD) is shown in the second thermalcycler body section 102. It is to be understood that there could be a simplified version of the thermalcycler described. This would be a unit without the guide tubes 105 where the sample tube is captured between the chamber halves and the heater film. This would be done in a system where there is not a requirement for being able to change the sample tubing.

Figure 3:
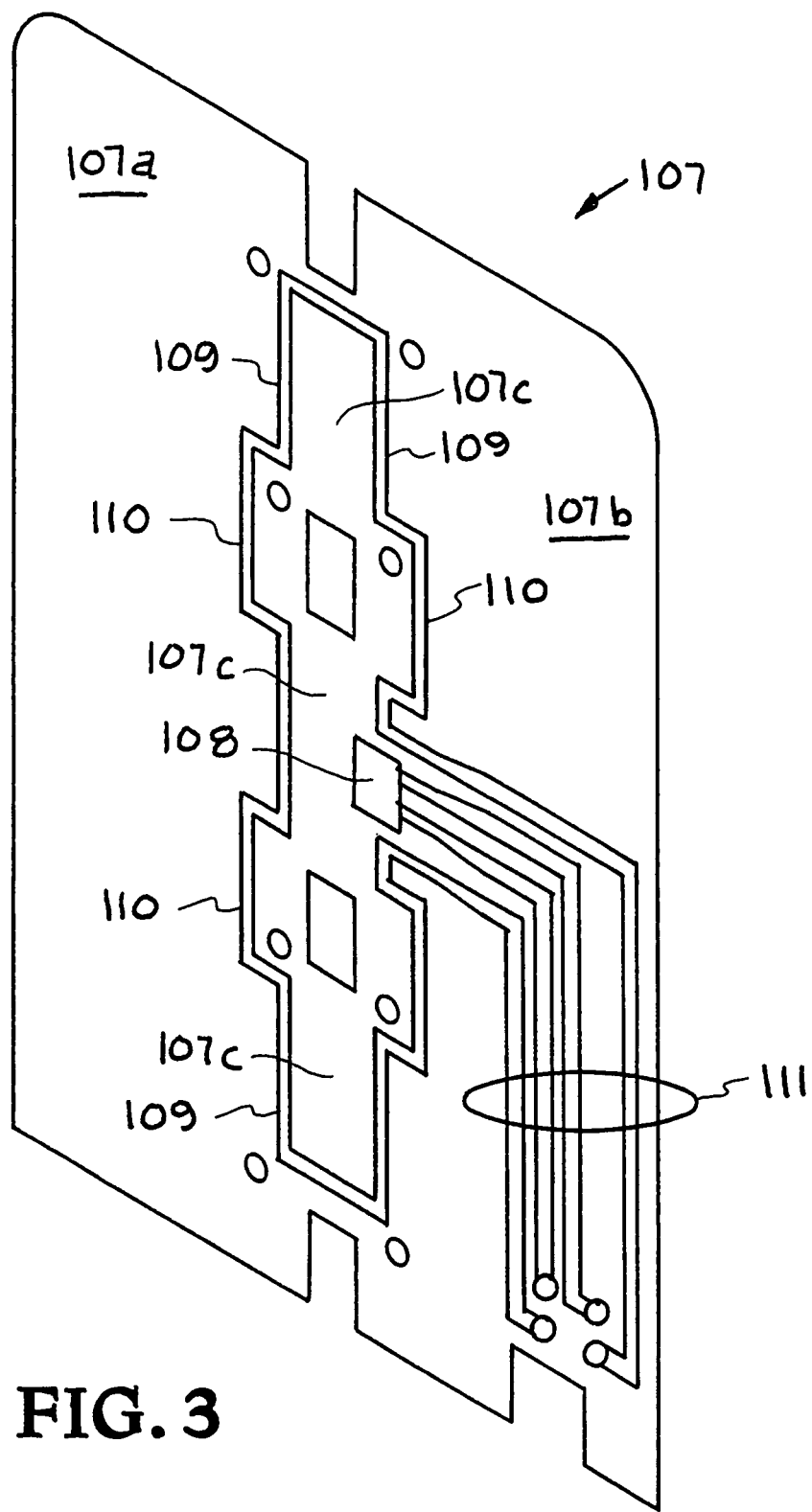

Referring specifically to FIG. 3, the support section of the thermalcycling system 100 is illustrated. The support section of the thermalcycling system 100 is a film support material section 107. When the thermalcycling system 100 is assembled the first copper chamber half 101 and the second copper chamber half 102 shown in FIGS. 1 and 2 will be positioned together against the support material section 107. The support material section 107 includes a left support section 107a and a right support section 107b. An intermediate support section 107c is between the left support section 107a and the right support section 107b. The intermediate support section 107c is adapted to receive the sample guide tubes 105. A RTD 108 is shown in the pocket for the RTD.

The film support material section 107 shown in FIG. 3 is a polyimide film support material section 107. Polyimide film is defined in ILC Dover, Film, Fiber & Textile Technology Terms & Definitions, on the website http://www.ilcdover.com/products/aerospace_defense/textileterms.htm as: "Normally infusible, colored (often amber) high performance polymers with predominantly aromatic molecules of high thermal stability. They have excellent high temperature properties and radiation resistance, inherently low flammability and smoke emission, low creep and high wear resistance. They have moderately high water absorption and are prone to hydrolysis and attack by alkalis and concentrated acids. A widely used form is Kapton® film, made in thicknesses from 0.008 to 0.125 mm. It has been used successfully in field applications where the environmental temperatures were as low as −269° C. and as high as 400° C. Polyimide film can be easily fabricated by a wide variety of techniques, including die cutting, punching and thermoforming. Applications include electrical insulation and thermal insulation. (Polyimide Film, Kapton, Kinel, Upilex, Upimol, Vespel)"

Specifically, the film support material section 107 shown in FIG. 3 is a Kapton polyimide film support material section 107. E. I. du Pont de Nemours and Company defines "Kapton® Polyimide Film" as: "DuPont™ Kapton® is a leader in the high performance films industry, offering over 40 years of diverse products, global technical support and customer service. DuPont has set a high standard in the polyimide film markets with its durability and performance in extreme temperature environments. Kapton® has a unique combination of electrical, thermal, chemical and mechanical properties and retains these properties over a wide range of industrial environments and applications. From miniaturized electronic components to Mars rover heaters, from high speed locomotive motors to airbag seat sensors, DuPont™ Kapton® polyimide films make innovative design solutions possible."

A heater trace is shown in the Kapton polyimide film support material section 107. The heater trace is used to heat the thermalcycler 100. The heater trace includes a Ni-chrom heater trace portion 109 and a conducting portion 110. Copper plated traces 111 for power and signal transmission are shown in the Kapton polyimide film support material section 107. The heater trace extends along a major portion of the Kapton polyimide film support material section 107. The heater trace extends along more than seventy five percent of the length of the Kapton polyimide film support material section 107.

Figure 4:
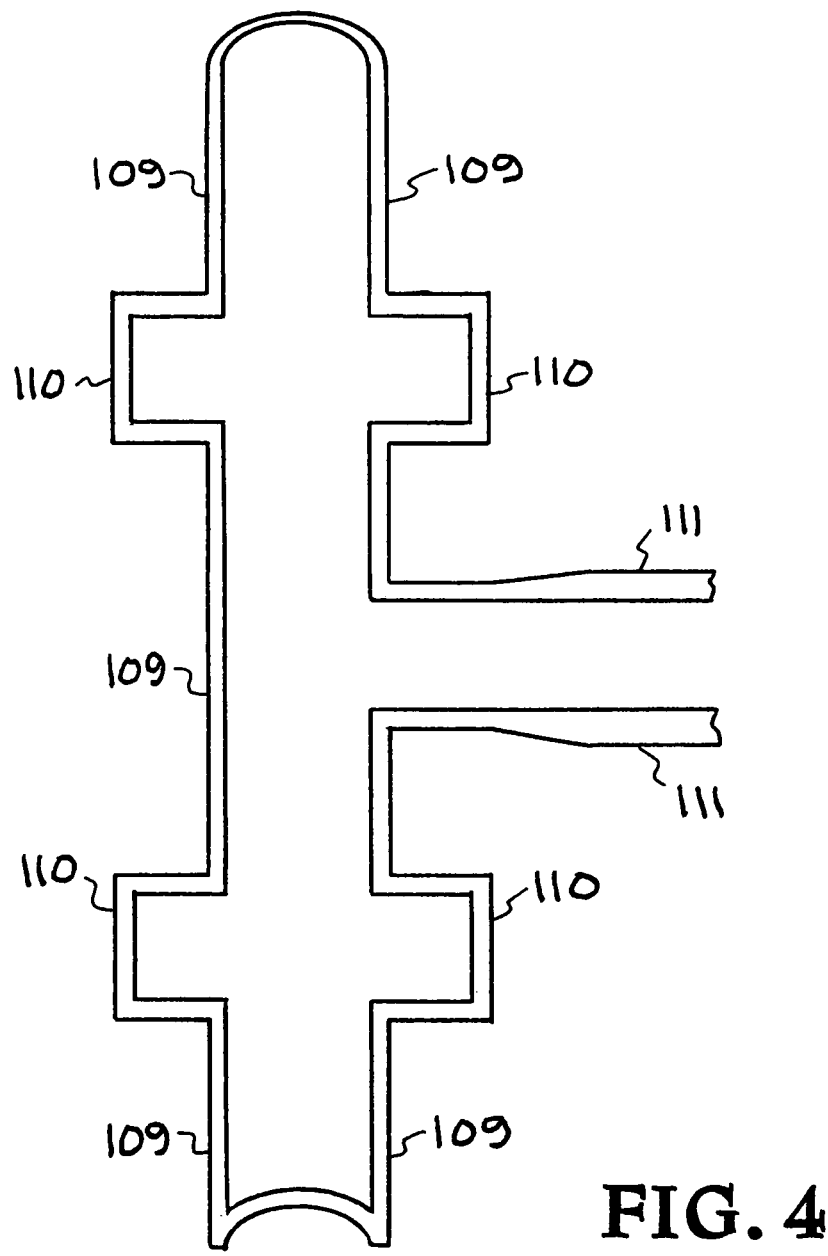

The heater trace is shown in greater detail in FIG. 4. The heater trace includes a Ni-chrom heater trace portion 109 and a conducting portion 110. The copper plated traces 111 are shown connected to the heater trace. The copper plated traces 111 provide power transmission for the heater trace.

Figure 5:
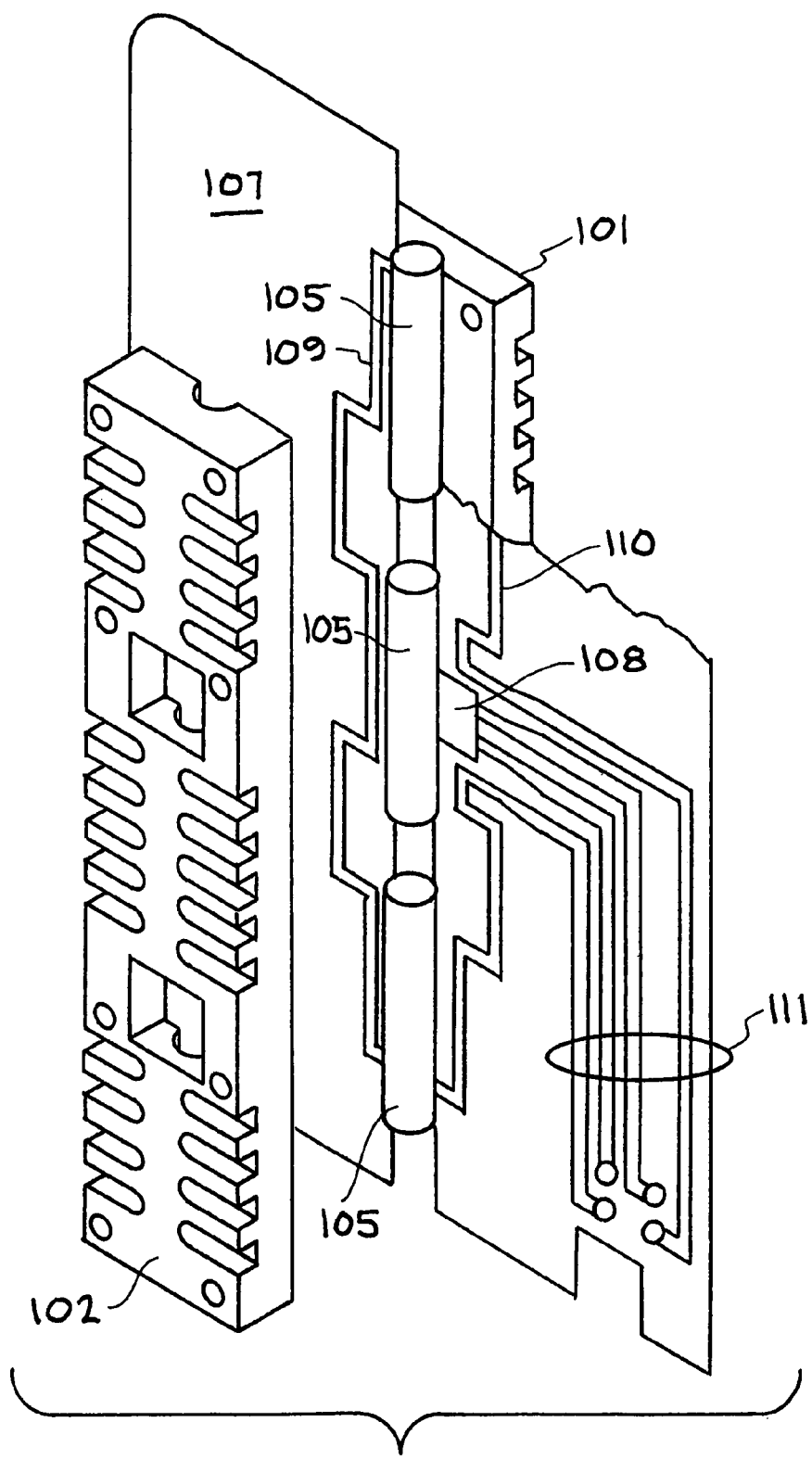

Referring specifically to FIG. 5, an illustration shows that the copper chamber half 101 is located on the back side of the polyimide film support material section 107. The copper chamber half 101 is shown in phantom behind the polyimide film support material section 107. The copper guide tubes 105 are show positioned against the polyimide film support material section 107. The copper chamber half 102 is shown ready to be positioned over the sample guide tubes 105 and positioned against the polyimide film support material section 107.

The RTD 108 is shown in the pocket for the RTD. The Ni-chrom heater trace portion 109 and the conducting portion 110 of the heater trace are shown in the Kapton polyimide film support material section 107. The copper plated traces 111 for power and signal transmission are shown in the Kapton polyimide film support material section 107.

Figure 6:
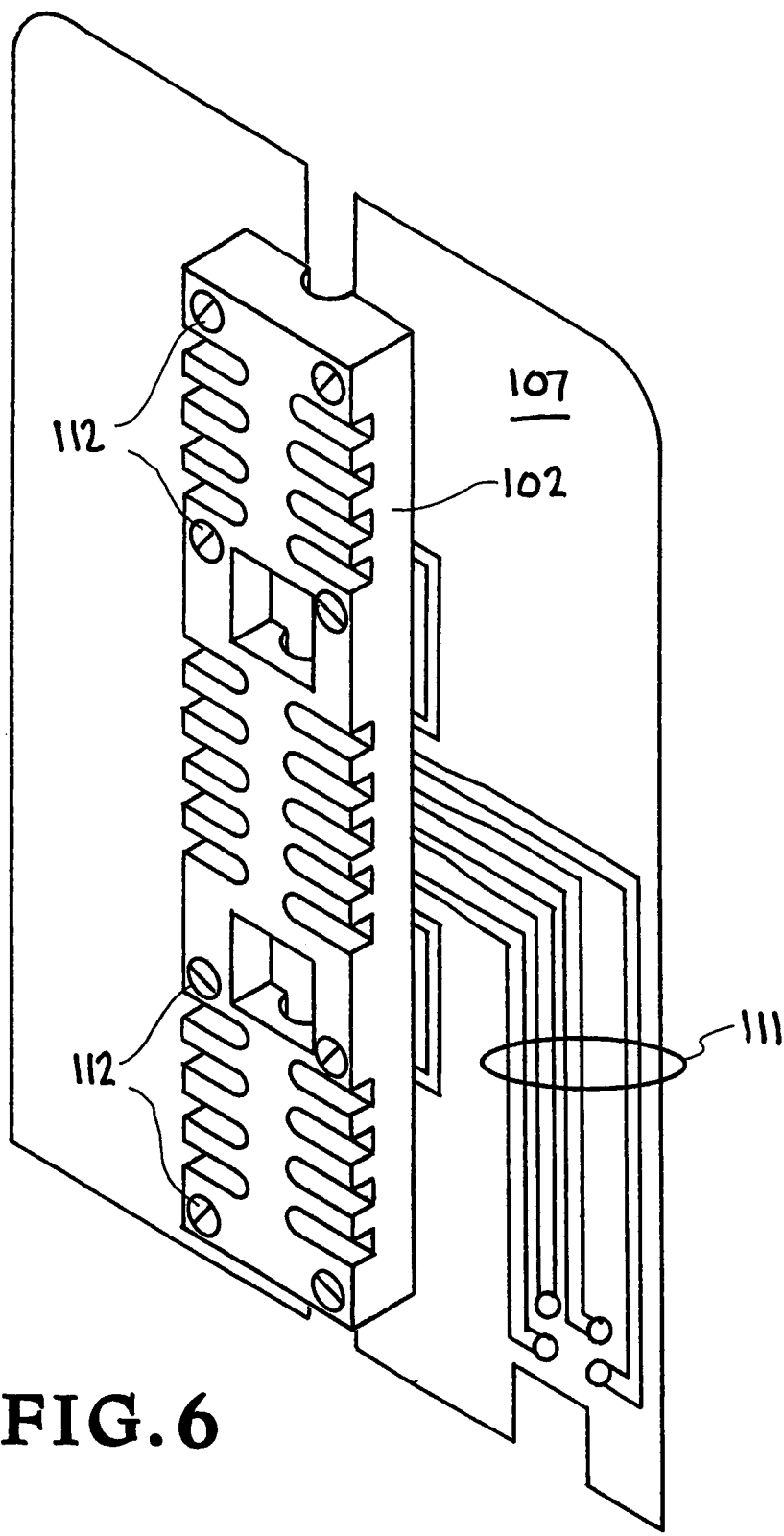

Referring specifically to FIG. 6, an illustration shows that the copper chamber half 102 has been positioned over the sample guide tubes 105. The copper chamber half 102 is positioned against the polyimide film support material section 107 in opposition to the copper chamber half 101 which is behind the copper chamber half 101.

Connectors connect the copper chamber half 102 to the copper chamber half 101 and the polyimide film support material section 107. Screw or bolts 112 are shown connecting the copper chamber half 102 to the polyimide film support material section 107 and the copper chamber half 101 which is behind the copper chamber half 101. The connector can be other types of connectors. For example the connectors can be solder connectors.

The Ni-chrom heater trace portion 109 and the conduction portion 110 of the heater trace are shown in the Kapton polyimide film support material section 107. The copper plated traces 111 for power and signal transmission are shown in the Kapton polyimide film support material section 107.

Figure 7:
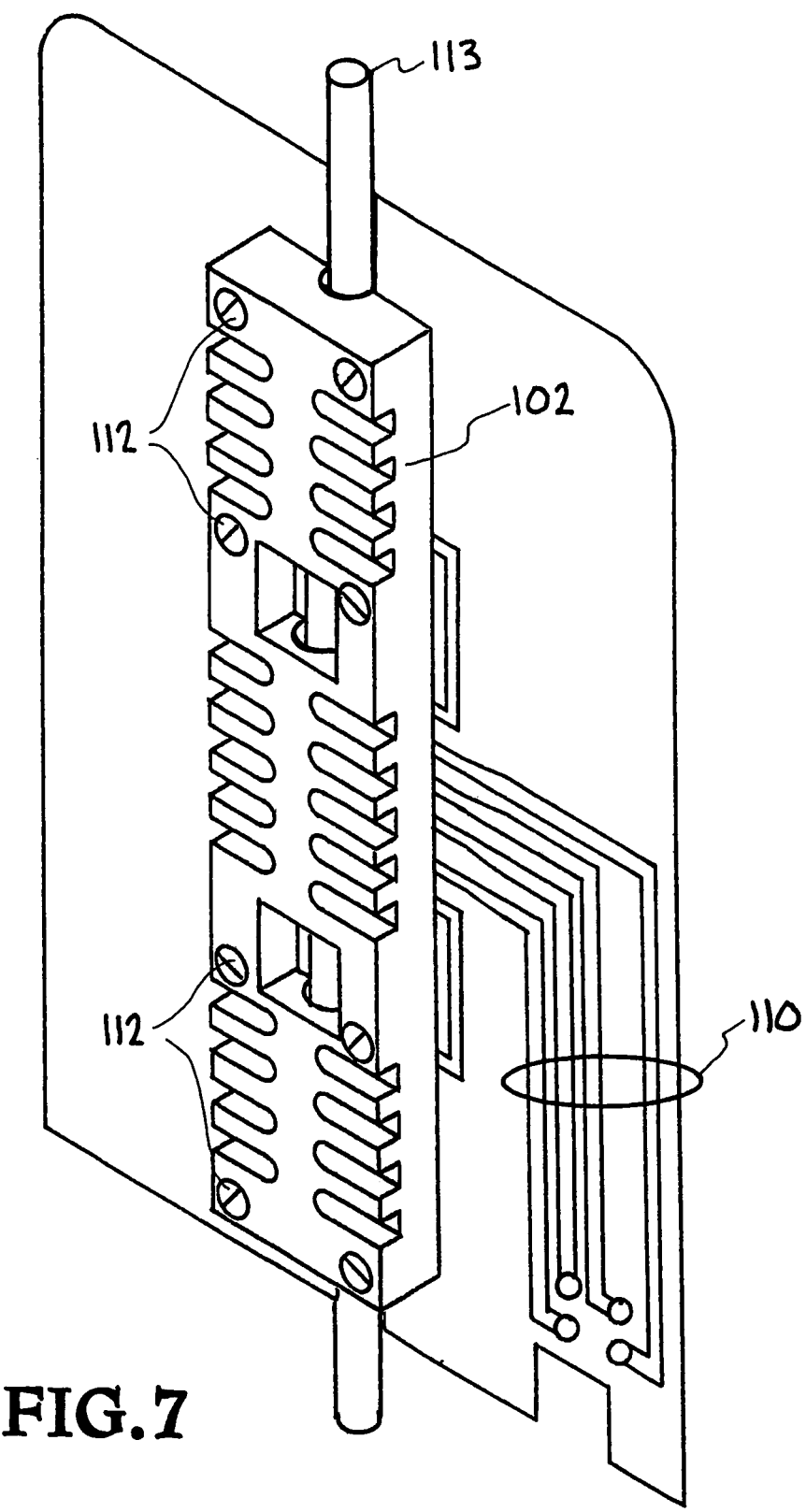

Referring specifically to FIG. 7, an illustration shows that a Teflon or polypropylene sample tube 113 has been inserted through the sample guide tubes 105. The copper chamber half 102 has been positioned over the sample guide tubes 105. The copper chamber half 102 is positioned against the polyimide film support material section 107. Screw or bolts 112 connect the copper chamber half 102 to the polyimide film support material section 107 and the copper chamber half 101 which is behind the copper chamber half 101. The copper plated traces 111 for power and signal transmission are shown in the Kapton polyimide film support material section 107. The Teflon or polypropylene sample tube 112 has been inserted through the sample guide tubes 105.

Referring now to FIGS. 1-7 the thermalcycling system 100 provides a method of constructing a thermalcycler. The method includes various steps. A polyimide film support section 107 is provided. A first thermalcycler body section 101 having a first face is provided. The first thermalcycler body section 101 is made of a material that is a good thermal conductor. A second thermalcycler body section 102 having a second face is provided. The second thermalcycler body section 102 is made of a material that is a good thermal conductor. A cavity (see cavities 103 and 104) is formed in at least one of the first face or the second face. A heater trace unit is connected to the support section, to the first thermalcycler body section 101, to the second thermalcycler body section 102, and to the thermalcycling unit 113. A thermalcycler unit 113 is operatively connected to the cavity, to the polyimide film support section 107, and to the heater trace unit 109/110. The first thermalcycler body section 101, the second thermalcycler body section 101, and the polyimide film support section 107 are positioned together wherein the first face and the second face are opposed to each other enclosing the heater trace unit 109/110 and the thermalcycler unit 113.

This embodiment of a thermalcycling system 100 illustrated in FIGS. 1-7 addresses the demonstrated need for a very portable and rapid instrument for doing PCR amplification. PCR amplification is becoming increasingly important. Autonomous detection systems incorporating PCR are being deployed. Applications of PCR amplification include point-of care diagnostics, rapid sequencing (e.g. forensics), environmental monitoring, and detection of bio-warfare/bio-terrorism agents in the field.

Accurate control of the temperature of the thermalcycler in which amplification reactions are performed is needed. Applicants have tested the temperature measurement and control of the thermalcycling system 100. The tests demonstrate the thermalcycling system 100 provides more precise temperature detection than prior thermalcycling systems. The tests demonstrate the thermalcycling system 100 performs better than other thermalcycling systems, particularly the temperature measurement and control of the thermalcycling system 100. Because the temperature sensor is completely inside the body of the chamber it gives a very accurate reading of the temperature of the chamber and thereby the sample. The chamber is thermally isolated from the rest of the hardware of the system because it is suspended on the thin kapton sheet. This combined with accurate temperature sensing and the fact that the heater element is also inside the chamber halves makes for a very thermally agile thermal-cycler. The chamber can change temperature very rapidly and be brought to the required temperature set points with great accuracy. This is extremely important when doing rapid PCR assays.

Figure 8:
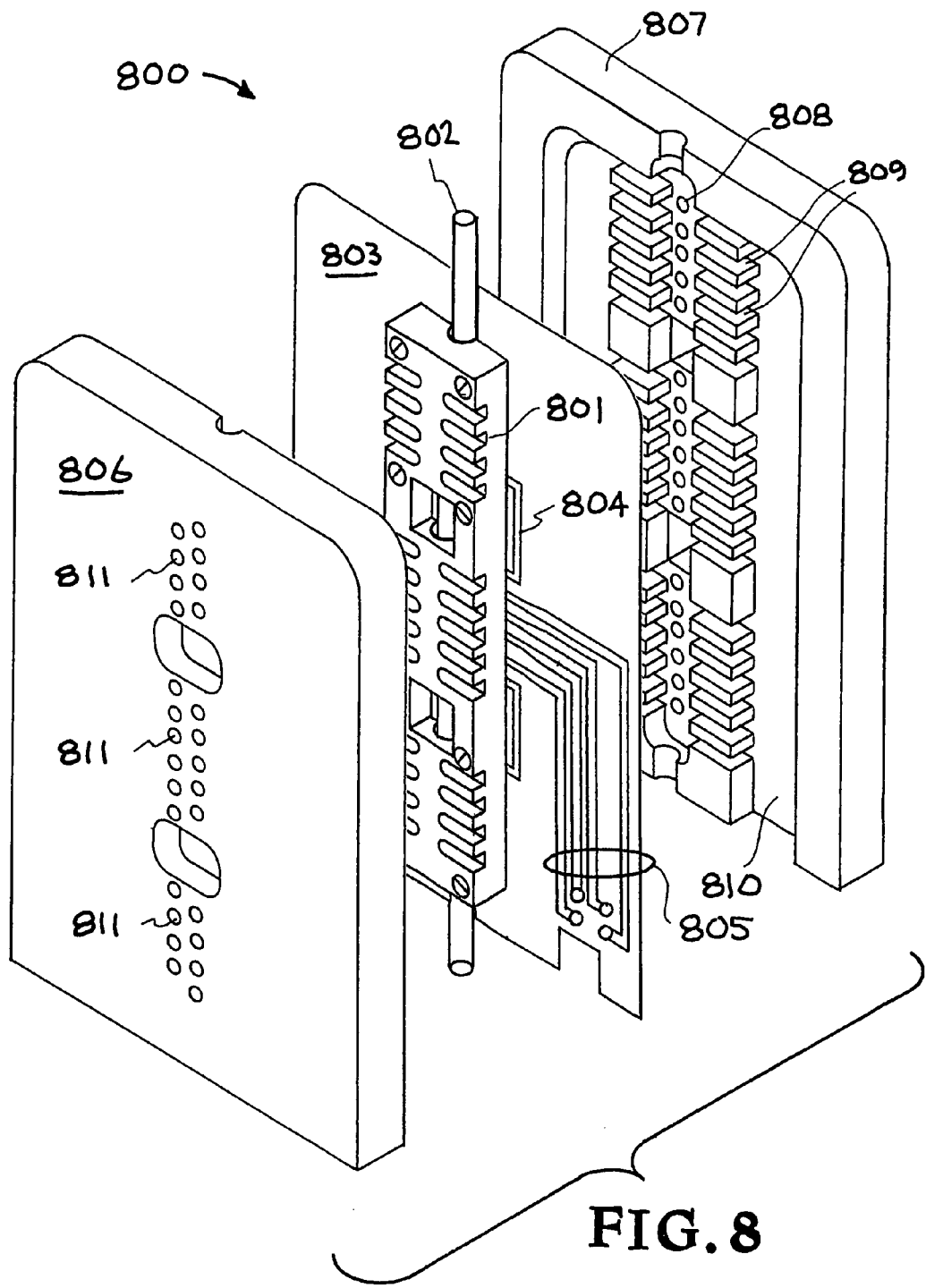
FIGS. 8 through 10 illustrate another embodiment of a thermalcycling system constructed in accordance with the present invention.
Figure 9:
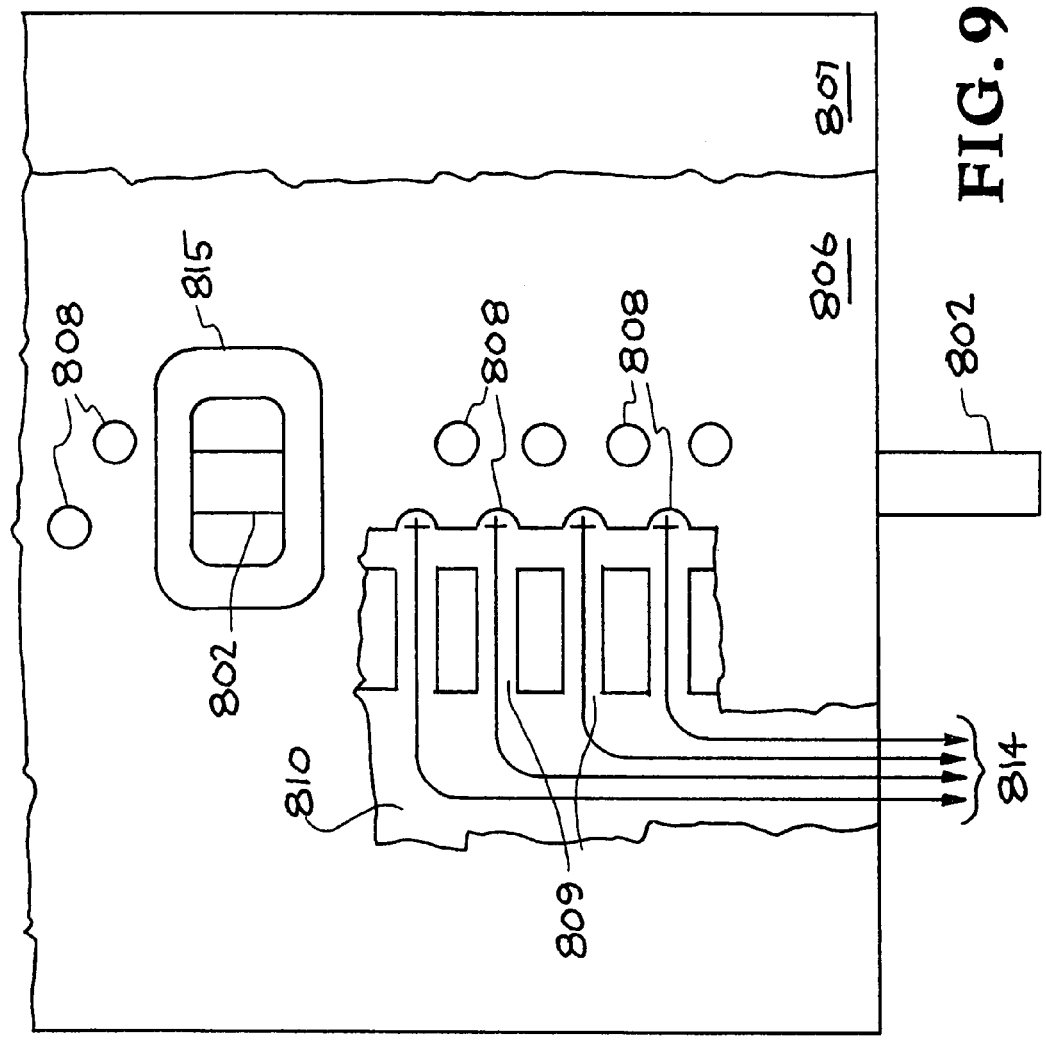
Figure 10:
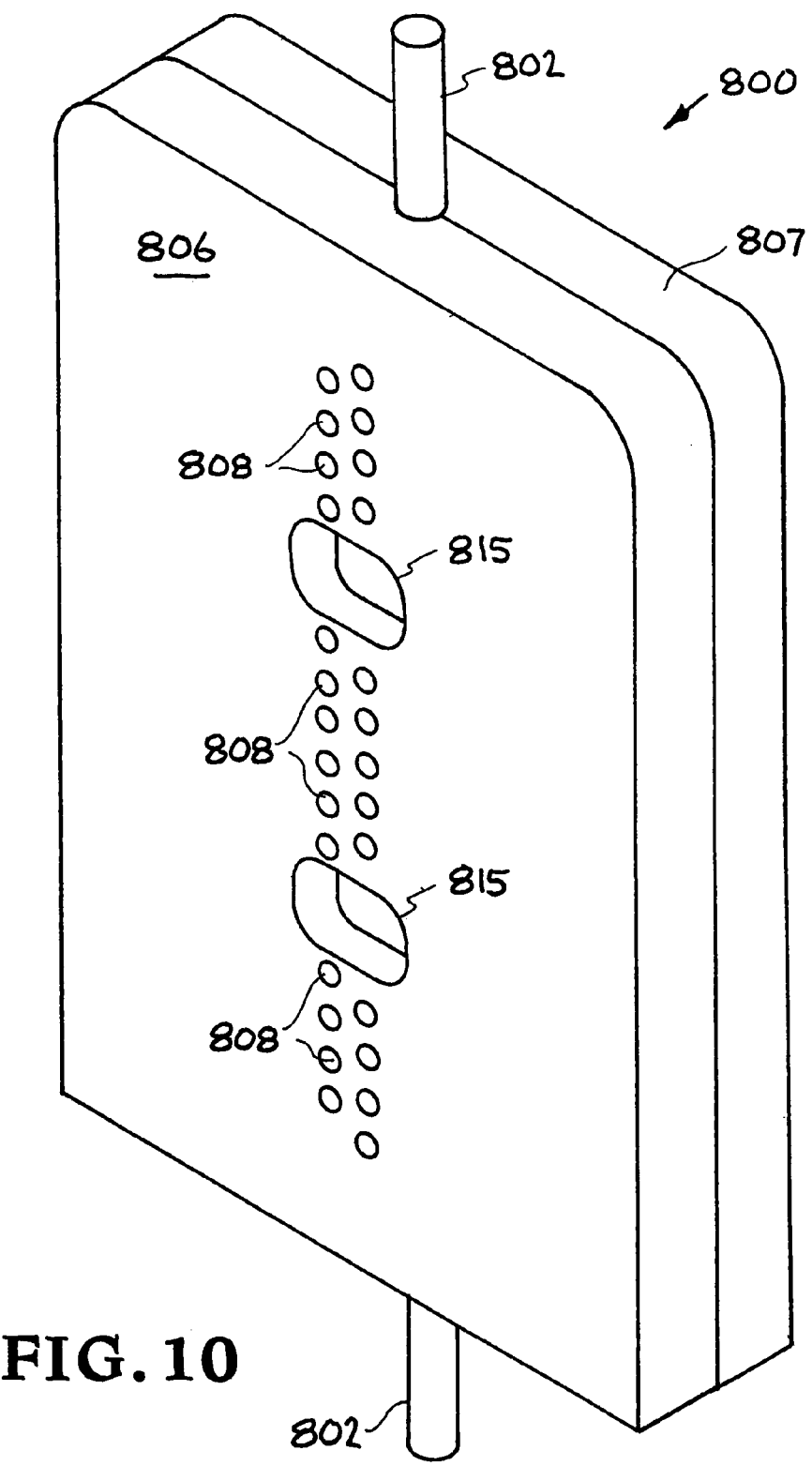

Referring now to FIGS. 8 through 10, the structural details and the operation of another embodiment of a thermalcycling system constructed in accordance with the present invention is illustrated. This embodiment of a thermalcycling system is designated generally by the reference numeral 800. The thermalcycling system 800 includes a first thermalcycler body section having a first face and a second thermalcycler body section having a second face. A cavity is formed by the first face and the second face. A thermalcycling unit is positioned in the cavity. A heater trace unit is connected to the support section, to the first thermalcycler body section, to the second thermalcycler body section, and to the thermalcycling unit. The first thermalcycler body section and the second thermalcycler body section are positioned together against the support section to enclose the thermalcycling unit and the heater trace unit. A temperature detector is integrated into the thermalcycler. A cooling jacket is positioned over the first thermalcycler body section, the second thermalcycler body section, the thermalcycling unit, the heater trace unit, and the temperature detector.

Referring specifically to FIG. 8, the thermalcycling system 800 includes a pair of mirror image body sections. The mirror image body sections are a first thermalcycler body section and a second thermalcycler body section. The first thermalcycler body section and the second thermalcycler body section are made of a material that is a good thermal conductor. The material that is a good thermal conductor has thermal conductivity. Wikipedia, the free encyclopedia defines "thermal conductivity." In physics, thermal conductivity, k, is the intensive property of a material that indicates its ability to conduct heat. It is defined as the quantity of heat, Q, transmitted in time t through a thickness L, in a direction normal to a surface of area A, due to a temperature difference ΔT, under steady state conditions and when the heat transfer is dependent only on the temperature gradient. Prior art thermal cyclers were constructed from silicon.

The first thermalcycler body section and the second thermalcycler body section of the thermalcycling system 800 illustrated in FIG. 8 are copper chamber halves. The first thermalcycler body section copper chamber half 801 is shown in FIG. 8. The second thermalcycler body section is also a copper chamber half and is located behind the copper chamber half 801. Copper provides good thermal conductivity. The first and second body copper chamber halves have internal cavities that receive a sample tube 802. The sample tube 802 is a Teflon or polypropylene sample tube.

The first and second body copper chamber halves are mounted on a support section 803. The support section 803 is a film support material. The film support material is a polyimide film support material. More specifically, the film support material section 803 shown in FIG. 8 is a Kapton polyimide film support material. A portion of the heater trace unit 804 is shown in the Kapton polyimide film support material section 803. The heater trace 804 is used to heat the thermalcycler 800. Copper plated traces 805 for power and signal transmission are shown in the Kapton polyimide film support material section 803.

A cooling jacket is positioned over the first and second body copper chamber halves, the heater trace unit, the temperature detector, the Kapton polyimide film support material section 803, and the sample tube 802. The cooling jacket includes a pair of mirror image cooling jacket sections 806 and 807. The mirror image cooling jacket sections 806 and 807 are made of a plastic or other suitable material. The mirror image cooling jacket sections 806 and 807 fit over and contain the first and second body copper chamber halves, the heater trace unit, the temperature detector, the Kapton polyimide film support material section 803, and the operating portion of the sample tube 802.

The mirror image cooling jacket sections 806 and 807 include a series of holes and grooves for channeling air flow through the thermalcycling system 800. The cooling jacket section 806 includes a series of holes 808 and a series of grooves 809. The series of grooves 809 connect with a pair of channels 810. The mirror image cooling jacket sections 806 and 807 include a series of holes and grooves for channeling air flow through the thermalcycling system 800. The cooling jacket section 807 includes a series of holes 811 and a series of grooves 812. The series of grooves 812 connect with a pair of channels 813. When the mirror image cooling jacket sections 806 and 807 are assembled over the first and second body copper chamber halves, the heater trace unit, the temperature detector, the Kapton polyimide film support material section 803, and the sample tube 802; the series of holes 808 and 811, the series of grooves 809 and 812, and the channels 810 and 813 channel air flow through the thermalcycling system 800 to cool the thermalcycling system 800 and improve polymerase chain reaction and other thermalcycling operations.

Referring now specifically to FIG. 9 an enlarged portion of the thermalcycling system 800 is shown. A portion of the cooling jacket sections 806 is cut away to show the series of holes 808, the series of grooves 809, and the channel 810. Air illustrated by the arrows 814 is directed through the series of holes 808, the series of grooves 809, and the channel 810. The series of holes 808, the series of grooves 809, and the channel 810 direct air flow through the thermalcycling system 800 to cool the thermalcycling system 800 and improve polymerase chain reaction and other thermalcycling operations. One of the windows 815 is shown in FIG. 9. The window 815 provides a view into the thermalcycling system 800 showing the sample tube 802. The windows of the thermalcycling system 800 provide optical access to the fluid within the tubing, enabling fluorescence detection for real time PCR and bubble detection with the incorporation of the heater in, for example, an LED/filter/detector optical assembly.

Referring now specifically to FIG. 10, the mirror image cooling jacket sections 806 and 807 are shown assembled over the copper chamber halves, the heater trace unit, the temperature detector, the support material section, and the sample tube 802. The mirror image cooling jacket sections 806 and 807 fit over and contain the first and second body copper chamber halves, the heater trace unit, the temperature detector, the Kapton polyimide film support material section, and the operating portion of the sample tube 802. The windows 815 provide a view into the thermalcycling system 800. The mirror image cooling jacket sections 806 and 807 include a series of holes and grooves for channeling air flow through the thermalcycling system 800. The cooling jacket section 806 includes the series of holes 808. The series of holes 808 connect with the grooves 809 and channels 810. The series of holes 808, the series of grooves 809, and the channels 810 direct air flow through the thermalcycling system 800 to cool the thermalcycling system 800 and improve polymerase chain reaction and other thermalcycling operations.

Figure 11:
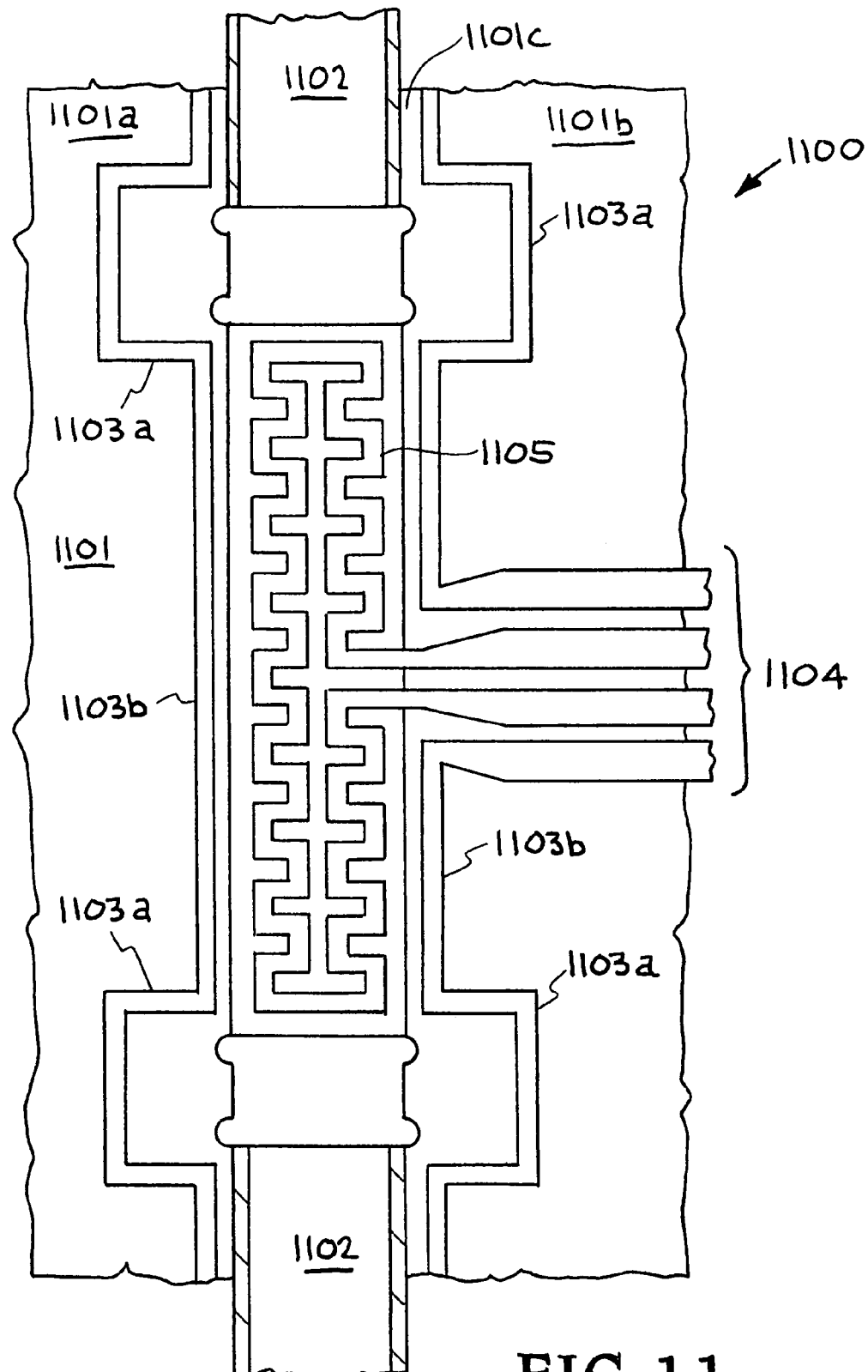
FIG. 11 illustrates another embodiment of a thermalcycling system constructed in accordance with the present invention.

Referring now to FIG. 11, the structural details and the operation of another embodiment of a thermalcycling system constructed in accordance with the present invention is illustrated. This embodiment of a thermalcycling system is designated generally by the reference numeral 1100. The thermalcycling system 1100 includes a first thermalcycler body section having a first face and a second thermalcycler body section having a second face. A cavity is formed by the first face and the second face. A thermalcycling unit is positioned in the cavity. A heater trace unit is connected to the support section, to the first thermalcycler body section, to the second thermalcycler body section, and to the thermalcycling unit. The first thermalcycler body section and the second thermalcycler body section are positioned together against the support section to enclose the thermalcycling unit and the heater trace unit. A temperature detector is integrated into the thermalcycler.

As shown in FIG. 11, the support section of the thermalcycling system is a film support material section 1101. When the thermalcycling system 1100 is assembled a first copper chamber half and a second copper chamber half similar to those shown in FIGS. 1 and 2 will be positioned together against the support material section 1101. The support material section 1101 includes a left support section 1101*a* and a right support section 1101*b*. An intermediate support section 1101*c* is between the left support section 1101*a* and the right support section 1101*b*. The intermediate support section 1101*c* is adapted to receive sample guide tubes 1102.

The film support material section 1101 is a polyimide film support material section 1101. More specifically, the film support material section 1101 shown is a Kapton polyimide film support material section 1101. A heater trace 1103 is shown in the Kapton polyimide film support material section 1101. The heater trace 1103 is used to heat the thermalcycler 1100. The heater trace 1103 includes a Ni-chrom heater trace portion 1103*a* and a conducting portion 1103*b*. Copper plated traces 1104 for power and signal transmission are shown in the Kapton polyimide film support material section 1101. The heater trace 1103 extends along a major portion of the Kapton polyimide film support material section 1101. The heater trace extends along more than seventy five percent of the length of the Kapton polyimide film support material section 1101.

A temperature detecting circuit 1105 is integrated into the thermalcycler 1100. Accurate control of the temperature of the thermalcycler 1100 in which amplification reactions are performed is needed. The temperature detecting circuit 1105 replaces the Resistance Temperature Detector (RTD) illustrated in the previous embodiments. The temperature detecting circuit 1105 is located on the intermediate support section 1101*c* and extends adjacent the sample guide tubes 1102. The thermalcycler 1100 accomplishes various operations including polymerase chain reaction, testing for DNA hybridization, isothermal reaction, nucleic acid sequence-based amplification, rolling-circle amplification, incubation for immunoassay, and other uses.

The present invention also provides a method of constructing a thermalcycler. The method incorporates the principle of the use of a highly conductive material and a distributed application of heat for providing a uniform temperature profile over the unique geometry of flow through PCR (necessarily a long thin tube to allow flow through) of the thermalcycler. The method includes various steps including providing a polyimide film support section; providing a first thermalcycler body section having a first face, the first thermalcycler body section made of a material that is a good thermal conductor; providing a second thermalcycler body section having a second face, the second thermalcycler body section made of a material that is a good thermal conductor; forming a cavity in at least one of the first face or the second face, positioning a heater trace unit connected to the support section, to the first thermalcycler body section, to the second thermalcycler body section, and to the thermalcycling unit; positioning a thermalcycler unit operatively connected to the cavity, to the polyimide film support section, and to the heater trace unit; and connecting the first thermalcycler body section, the second thermalcycler body section, and the polyimide film support section together; wherein the first face and the second face are opposed to each other enclosing the heater trace unit and the thermalcycler unit and wherein the first thermalcycler body section made of a material that is a good thermal conductor and the second thermalcycler body section made of a material that is a good thermal conductor enclose the heater trace unit and the thermalcycler unit and provide a distributed application of heat and a uniform temperature profile over the thermalcycler.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A thermal cycler, comprising:
a first thermalcycler body section having a first face, said first thermalcycler body section made of a material that has the thermal conductivity of metals;
a second thermalcycler body section having a second face, said second thermalcycler body section made of a material that has the thermal conductivity of metals;
a cavity formed by said first face and said second face;
a thermalcycling unit positioned in said cavity immediately adjacent and contacting said first face and said second face;
a film support material section having a heater trace in said film support material section wherein said film support material section having a heater trace is connected to said first thermalcycler body section, to said second thermalcycler body section, and to said thermalcycling unit, said film support material section having a heater trace located between said first face and said second face and contacting said first face and said second face;
wherein said first thermalcycler body section and said second thermalcycler body section are positioned together to enclose said thermalcycling unit and said film support material section having a heater trace;
connectors connecting said first thermalcycler body section and said second thermalcycler body section; and
a cooling jacket positioned over said first thermalcycler body section, said second thermalcycler body section, and said thermalcycling unit to cool said first thermalcycler body section, said second thermalcycler body section, and said thermalcycling unit.

2. The thermal cycler apparatus of claim 1 wherein said film support material section having a heater trace is a polyimide film support section that has a length and wherein said heater trace extends along more than seventy five percent of said length of said polyimide film support section.

3. The thermal cycler apparatus of claim 1 wherein said film support material section having a heater trace unit is a nickel alloy heater trace unit.

4. The thermal cycler apparatus of claim 1 wherein said first thermalcycler body section and said second thermalcycler body section are copper chamber halves.

5. The thermal cycler apparatus of claim 1 wherein said thermalcycling unit comprises sample guide tubes and a sample tube positioned within said sample guide tubes.

6. The thermal cycler apparatus of claim 5 wherein said sample tube is a polypropylene sample tube.

7. The thermal cycler apparatus of claim 1 including a resistance temperature detector connected to said support section and said thermalcycling unit.

8. The thermal cycler apparatus of claim 1 wherein said connectors connecting said first thermalcycler body section and said second thermalcycler body section are screw or bolts connecting said first thermalcycler body section and said second thermalcycler body section.

9. The thermal cycler apparatus of claim 1 wherein said cooling jacket includes a pair of mirror image cooling jacket sections with holes, grooves, and channels for cooling the thermal cycler apparatus.

10. A thermal cycler apparatus, consisting of:
a first thermalcycler body section having a first face, said first thermalcycler body section made of a material that has the thermal conductivity of metals;
a second thermalcycler body section having a second face, said second thermalcycler body section made of a material that has the thermal conductivity of metals;
a cavity formed by said first face and said second face;
a thermalcycling unit positioned in said cavity;
a polyimide film support section having a heater trace in said polyimide film support section, wherein said polyimide film support section having a heater trace is connected to said first thermalcycler body section, to said second thermalcycler body section, and to said thermalcycling unit, said polyimide film support section having a heater trace located between said first face and said second face and contacting said first face and said second face;
wherein said first thermalcycler body section and said second thermalcycler body section are positioned together against said support section to enclose said thermalcycling unit and said polyimide film support section having a heater trace;
connectors connecting said first thermalcycler body section and said second thermalcycler body section; and
a cooling jacket positioned over said first thermalcycler body section, said second thermalcycler body section, and said thermalcycling unit to cool said first thermalcycler body section, said second thermalcycler body section, and said thermalcycling unit.

11. The thermal cycler apparatus of claim 10 wherein said polyimide film support section has a length and wherein said heater trace extends along more than seventy five percent of said length of said polyimide film support section and wherein said heater trace is a nickel alloy heater trace.

12. The thermal cycler apparatus of claim 10 wherein said first thermalcycler body section and said second thermalcycler body section are copper chamber halves.

13. The thermal cycler apparatus of claim 10 wherein said thermalcycling unit comprises sample guide tubes and a sample tube positioned within said sample guide tubes.

14. The thermal cycler apparatus of claim 13 wherein said sample tube is a polypropylene sample tube.

15. The thermal cycler apparatus of claim 10 including a resistance temperature detector connected to said support section and said thermalcycling unit.

16. The thermal cycler apparatus of claim 10 wherein said cooling jacket positioned over said first thermalcycler body section, said second thermalcycler body section, and said thermalcycling unit includes a flow channel including holes and grooves in said first thermalcycler body section and said second thermalcycler body section.

17. The thermal cycler apparatus of claim 10 wherein said cooling jacket includes a pair of mirror image cooling jacket sections with holes, grooves, and channels for cooling the thermal cycler apparatus.

18. A method of constructing a thermalcycler, comprising the steps of:
providing a polyimide film support section having a heater trace;
providing a first thermalcycler body section having a first face, said first thermalcycler body section made of a material that has the thermal conductivity of metals;

providing a second thermalcycler body section having a second face, said second thermalcycler body section made of a material that has the thermal conductivity of metals;

forming a cavity in at least one of said first face or said second face, positioning said polyimide film support section having a heater trace between said first face of said first thermalcycler body section and said second face of said second thermalcycler body section, wherein said polyimide film support section having a heater trace is connected to said first thermalcycler body section, to said second thermalcycler body section, and to said thermalcycling unit;

positioning a thermalcycler unit operatively connected to said cavity, to said polyimide film support section having a heater trace and locating said polyimide film support section having a heater trace between said first face and said second face and contacting said first face and said second face;

connecting said first thermalcycler body section, said second thermalcycler body section, and said polyimide film support section having a heater trace together;

wherein said first face and said second face are opposed to each other enclosing said polyimide film support section having a heater trace and said thermalcycler unit; and positioning a cooling jacket over said first thermalcycler body section, said second thermalcycler body section, and said thermalcycling unit to cool said first thermalcycler body section, said second thermalcycler body section, and said thermalcycling unit.

19. The method of constructing a thermalcycler of claim 18 including a step of positioning a resistance temperature detector connected to said polyimide film support section and said thermalcycler unit.

20. A method of constructing a thermalcycler, comprising the steps of:

providing a polyimide film support section having a heater trace;

providing a first thermalcycler body section having a first face, said first thermalcycler body section made of a material that has the thermal conductivity of metals;

providing a second thermalcycler body section having a second face, said second thermalcycler body section made of a material that has the thermal conductivity of metals;

forming a cavity in at least one of said first face or said second face, positioning said polyimide film support section having a heater trace connected to said support section, to said first thermalcycler body section, to said second thermalcycler body section, and to said thermalcycling unit and locating said polyimide film support section having a heater trace unit between said first face and said second face and contacting said first face and said second face;

positioning a thermalcycler unit operatively connected to said cavity, to said polyimide film support section having a heater trace; and connecting said first thermalcycler body section, said second thermalcycler body section, and said polyimide film support section having a heater trace together;

wherein said first face and said second face are opposed to each other enclosing said polyimide film support section having a heater trace and said thermalcycler unit; and positioning a cooling jacket over said first thermalcycler body section, said second thermalcycler body section, and said thermalcycling unit to cool said first thermalcycler body section, said second thermalcycler body section, and said thermalcycling unit, wherein said first thermalcycler body section made of a material that has the thermal conductivity of metals and said second thermalcycler body section made of a material that has the thermal conductivity of metals and said cooling jacket enclose said polyimide film support section having a heater trace and said thermalcycler unit and provide a distributed application of heat and cooling and a uniform temperature profile over the thermalcycler.

* * * * *